(12) United States Patent  (10) Patent No.: US 7,578,812 B2
Datta et al.  (45) Date of Patent: Aug. 25, 2009

(54) PRE-FASTENED ABSORBENT ARTICLE HAVING SIMPLIFIED FASTENING FEATURES

(75) Inventors: Paul Joseph Datta, Appleton, WI (US); Robert Eugene Vogt, Neenah, WI (US); Thomas Walter Odorzynski, Green Bay, WI (US); Cassandra Elizabeth Morris, Charlottesville, VA (US); Jennifer Elizabeth Pozniak, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 552 days.

(21) Appl. No.: 10/017,894

(22) Filed: Dec. 14, 2001

(65) Prior Publication Data

US 2002/0138064 A1  Sep. 26, 2002

Related U.S. Application Data

(60) Provisional application No. 60/272,548, filed on Mar. 1, 2001.

(51) Int. Cl.
*A61F 13/68* (2006.01)
*A61F 13/62* (2006.01)

(52) U.S. Cl. ....................... 604/391; 604/394

(58) Field of Classification Search ................. 604/391, 604/385.29, 385.3, 389–390, 394–396, 385.03
See application file for complete search history.

(56) References Cited

U.S. PATENT DOCUMENTS

| 3,950,824 A | 4/1976 | Karami |
| 4,055,181 A | 10/1977 | Tritsch |
| 4,204,534 A | 5/1980 | Leary |
| 4,244,368 A | 1/1981 | Caradonna |
| 4,568,344 A | 2/1986 | Suzuki et al. |
| 4,615,084 A | 10/1986 | Erb |
| 4,615,695 A | 10/1986 | Cooper |
| 4,663,220 A | 5/1987 | Wisneski et al. |
| 4,699,622 A | 10/1987 | Toussant et al. |
| 4,704,116 A | 11/1987 | Enloe |
| 4,798,603 A | 1/1989 | Meyer et al. |
| 4,834,742 A | 5/1989 | Wilson et al. |
| 4,894,060 A | 1/1990 | Nestegard |
| 4,895,569 A | 1/1990 | Wilson et al. |
| 4,923,456 A | 5/1990 | Proxmire |

(Continued)

FOREIGN PATENT DOCUMENTS

DE  196 41 849  4/1998

(Continued)

OTHER PUBLICATIONS

Tappi Official Test Method T 543 om-94, "Bending Resistance of Paper (Gurley Type Tester)," published by the Tappi Press, Atlanta, Georgia, pp. 1-7.

*Primary Examiner*—Karin M Reichle
(74) *Attorney, Agent, or Firm*—H. Michael Kubicki

(57) ABSTRACT

Prefastened absorbent articles (20) may include a singular fastening mechanism that includes an oversized fastener (60), to provide stability between the front waist region and the back waist region and to maintain the prefastened configuration. The prefastened absorbent articles can include a multiple property fastener (60) that has at least one engagement zone (65) and at least one non-abrasive zone (67).

15 Claims, 9 Drawing Sheets

U.S. PATENT DOCUMENTS

| | | | |
|---|---|---|---|
| 4,931,344 A | 6/1990 | Ogawa et al. | |
| 4,936,840 A | 6/1990 | Proxmire | |
| 4,946,527 A | 8/1990 | Battrell | |
| 5,026,364 A | 6/1991 | Robertson | |
| 5,051,259 A | 9/1991 | Olsen et al. | |
| 5,053,028 A | 10/1991 | Zoia et al. | |
| 5,087,253 A | 2/1992 | Cooper | |
| 5,112,326 A | 5/1992 | Quadrini | |
| 5,176,668 A | 1/1993 | Bernardin | |
| 5,176,670 A | 1/1993 | Roessler et al. | |
| 5,176,671 A | 1/1993 | Roessler et al. | |
| 5,176,672 A | 1/1993 | Bruemmer et al. | |
| 5,192,606 A | 3/1993 | Proxmire et al. | |
| 5,221,276 A | 6/1993 | Battrell | |
| 5,226,992 A | 7/1993 | Morman | |
| 5,269,776 A | 12/1993 | Lancaster et al. | |
| 5,300,058 A | 4/1994 | Goulait et al. | |
| 5,324,279 A | 6/1994 | Lancaster et al. | |
| 5,326,415 A * | 7/1994 | Thomas et al. | 156/244.11 |
| 5,342,344 A | 8/1994 | Lancaster et al. | |
| 5,358,500 A | 10/1994 | Lavon et al. | |
| 5,392,498 A | 2/1995 | Goulait et al. | |
| 5,399,219 A | 3/1995 | Roessler et al. | |
| 5,403,302 A | 4/1995 | Roessler et al. | |
| 5,473,800 A | 12/1995 | Hatomoto et al. | |
| 5,509,915 A | 4/1996 | Hanson et al. | |
| 5,531,732 A | 7/1996 | Wood | |
| 5,545,159 A | 8/1996 | Lancaster et al. | |
| 5,586,371 A | 12/1996 | Thomas | |
| 5,622,578 A | 4/1997 | Thomas | |
| 5,624,428 A | 4/1997 | Sauer | |
| 5,624,429 A | 4/1997 | Long et al. | |
| 5,626,573 A | 5/1997 | Igaue et al. | |
| 5,636,414 A * | 6/1997 | Litchholt | 24/304 |
| 5,643,242 A | 7/1997 | Lavon et al. | |
| 5,643,916 A | 7/1997 | Audia et al. | |
| 0,001,674 A * | 8/1997 | Ames et al. | 604/389 |
| 5,656,111 A | 8/1997 | Dilnik et al. | |
| 5,660,666 A | 8/1997 | Dilnik et al. | |
| 5,664,302 A | 9/1997 | Thomas | |
| 5,665,084 A * | 9/1997 | Richmond | 604/389 |
| 5,676,652 A | 10/1997 | Hunter et al. | |
| 5,692,271 A | 12/1997 | Provost et al. | |
| 5,695,868 A | 12/1997 | McCormack | |
| 5,702,797 A | 12/1997 | Sakakibara et al. | |
| 5,704,933 A | 1/1998 | Fell et al. | |
| 5,722,127 A | 3/1998 | Coates | |
| 5,782,819 A | 7/1998 | Tanzer et al. | |
| 5,843,056 A | 12/1998 | Good et al. | |
| 5,846,262 A | 12/1998 | Sayama et al. | |
| 5,897,545 A | 4/1999 | Kline et al. | |
| 5,924,133 A | 7/1999 | Zapiti | |
| 5,926,926 A | 7/1999 | Kato | |
| 5,938,997 A | 8/1999 | Sakakibara et al. | |
| 5,948,337 A | 9/1999 | Sakakibara et al. | |
| 5,953,797 A | 9/1999 | Provost et al. | |
| 5,957,908 A | 9/1999 | Kline et al. | |
| 5,961,761 A | 10/1999 | Heindel et al. | |
| 5,968,030 A | 10/1999 | Shimizu et al. | |
| 5,997,522 A | 12/1999 | Provost et al. | |
| 6,022,432 A | 2/2000 | Elsberg et al. | |
| 6,036,805 A | 3/2000 | McNichols | |
| 6,076,238 A * | 6/2000 | Arsenault et al. | 24/452 |
| 6,099,516 A * | 8/2000 | Pozniak et al. | 604/386 |
| 6,132,660 A * | 10/2000 | Kampfer | 264/167 |
| 6,149,934 A | 11/2000 | Krzysik et al. | |
| 6,180,205 B1 * | 1/2001 | Tachauer et al. | 428/100 |
| 6,210,389 B1 | 4/2001 | Long et al. | |
| 6,276,032 B1 * | 8/2001 | Nortman et al. | 24/572.1 |
| 6,287,287 B1 | 9/2001 | Elsberg | |
| 6,352,528 B1 * | 3/2002 | Weber et al. | 604/385.03 |
| 6,447,497 B1 * | 9/2002 | Olson | 604/389 |
| 6,454,752 B1 * | 9/2002 | Huang et al. | 604/389 |
| 6,489,004 B1 * | 12/2002 | Martin et al. | 428/100 |
| 6,552,245 B1 * | 4/2003 | Roessler et al. | 604/367 |
| 6,554,816 B1 * | 4/2003 | Olson | 604/386 |
| 6,645,190 B1 * | 11/2003 | Olson et al. | 604/389 |
| 2002/0099353 A1 * | 7/2002 | Olson | 604/389 |
| 2002/0116799 A1 * | 8/2002 | Martin et al. | 24/452 |

FOREIGN PATENT DOCUMENTS

| | | |
|---|---|---|
| EP | 0 080 152 | 6/1983 |
| EP | 0 217 032 | 4/1987 |
| EP | 0 276 557 | 8/1988 |
| EP | 0 689 821 | 1/1996 |
| EP | 0 780 109 | 6/1997 |
| EP | 0 800 379 | 10/1997 |
| EP | 0 951 888 | 10/1999 |
| EP | 988808 A1 * | 3/2000 |
| FR | 2 764 297 | 12/1998 |
| JP | 2880606 | 4/1999 |
| WO | 94/13236 | 6/1994 |
| WO | 95/05140 | 2/1995 |
| WO | 95/16425 | 6/1995 |
| WO | 95/27460 | 10/1995 |
| WO | 97/48357 | 12/1997 |
| WO | 99/07319 | 2/1999 |
| WO | 99/23986 | 5/1999 |
| WO | 99/23987 | 5/1999 |
| WO | 99/32062 | 7/1999 |
| WO | 99/33425 | 7/1999 |
| WO | 99/38929 | 8/1999 |
| WO | 00/15069 | 3/2000 |
| WO | WO 0037016 A1 * | 6/2000 |
| WO | 00/50229 | 8/2000 |
| WO | 01/43683 | 6/2001 |
| WO | 01/70155 | 9/2001 |

* cited by examiner

PRE-FASTENED ABSORBENT ARTICLE HAVING SIMPLIFIED FASTENING FEATURES

The present application claims the benefit of the filing date of U.S. Provisional Patent Application Ser. No. 60/272,548 filed on Mar. 1, 2001 and entitled "A Pre-Fastened Absorbent Article Having Improved Fit and Fastening Features".

BACKGROUND OF THE INVENTION

The present invention relates to disposable absorbent articles that are adapted to contain body exudates. More particularly, the present invention relates to prefastened disposable absorbent articles having simplified fastening features. The simplified fastening features provide benefits in the areas of skin-friendliness (i.e. reduced abrasiveness) and the stability of the closure provided by the fastening features.

Absorbent articles such as diapers, training pants or incontinence garments desirably provide a close, comfortable fit about the wearer and contain body exudates. Disposable absorbent articles can be secured about the wearer by a variety of fastening systems. When disposable absorbent articles are provided in a prefastened configuration, manufacturing benefits can be obtained by simplifying the manner in which the article is prefastened.

Desirably, absorbent articles, after being soiled, can be removed from the wearer in a convenient and clean manner without undesirably soiling the caregiver, the wearer, the surrounding area or the clothes of the wearer. In certain circumstances, it is also beneficial for such absorbent articles to have "pant-like" features and to be capable of being pulled up or down over the hips of the wearer to allow the wearer or caregiver to easily pull the article on and easily remove the article if it has not been soiled. Given the various shapes and sizes of wearers of absorbent articles, it would also be beneficial for the caregiver or the wearer to be able to adjust the fit of the waist area of the article. These benefits can be provided by an absorbent article that is prefastened. For example, such absorbent articles can be used with active infants and toddlers.

Conventional diapers are not provided in a "prefastened" condition and have typically included a front waist portion and a back waist portion that are releasably connected about the hips of the wearer during use by conventional fasteners such as adhesive tape fasteners or hook and loop fasteners. For example, conventional fasteners typically included a pair of fasteners, such as adhesive tape tabs, located on the outermost corners of the diaper in the back waist region of the diaper and a complimentary fastener, such as a taping panel, located on the exterior surface of the outer cover of the diaper in the front waist portion of the diaper. In such a configuration, the diaper has been positioned between the legs of the wearer while the wearer is lying down and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the caregiver. However, such conventional diapers are not provided in a pant-like, prefastened configuration and, thus, are not configured to be pulled up or down over the hips of the wearer when the fasteners are attached. Moreover, the fasteners on such conventional diapers generally must be disengaged and reattached to further conform the waist portions of the diaper to the wearer. Such disengagement and reattachment for adjustment can be difficult to accomplish when the wearer is active or resisting changing of the diaper.

Consequently, use of prefastened absorbent articles can overcome these deficiencies. While the ease of application/removal and conformed fit benefits can be enjoyed when the prefastened diaper is applied as a pant (and the wearer is standing up), the prefastened diaper desirably is convertible between pant and diaper configurations. Covertibility means that the prefastened diaper can be applied as either a pull-on pant (like a training pant) or a diaper—depending on the occasion or needs of the users. The prefastened diaper can also be removed as either a pull-on pant or a diaper. Therefore, it is necessary for the prefastened diaper to be conveniently convertible between these two configurations.

Several attempts have been made to provide absorbent articles that effectively contain body exudates, are capable of being pulled up or down over the hips of the wearer and provide ease of cleaning and removal after being soiled. For example, some conventional absorbent articles, such as conventional training pants, have included integral side panels that connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled. With respect to prefastened diapers, the stretchable side panels have been replaced by extended front and rear ear portions that are bonded together to form side bonded areas. In some instances, the side bonds are intended to be passive side bonds that are readily tearable so that the prefastened diaper achieves the desired convertibility. In addition to permitting the convertibility of the article between diaper and pant, the side bonds are typically also necessary to maintain stability between the front and back waist regions so that the article remains prefastened when applied as a pant. Processes have been developed for manufacturing prefastened articles having side bonds, but they typically include additional processing steps, equipment and materials.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely, which can undesirably result in leaks. As a result, many of such articles have not contained bodily exudates as effectively as conventional diaper-type articles that can be adjusted to achieve a more conforming fit to the wearer. Moreover, the inspection and removal of soiled absorbent articles that have integral side panels, such as conventional training pants, have not always been completely satisfactory. For example, the side panels have been difficult to tear when attempting to remove the article from the waist of the wearer instead of pulling the article down over the hips of the wearer.

Both conventional diapers and pant-like, prefastened articles can utilize fastening features that include hook and loop fasteners. The hook component of the fastening feature typically includes a series or grouping of individual hook elements attached to a hook backing material. The hook component is typically applied to a longitudinal edge portion of the article, such as a front or rear ear area of the article. Typically, the hook component is positioned so as to be able to perform the function of securing the article about the waist of the wearer. Of course, the hook component can be positioned to accomplish additional purposes such as securing the article about the legs of the wearer or providing other adjustments related to the fit of the article. The loop component of the fastening feature is typically situated so as to provide convenient engagement for the hook component. The loop component can be an independent component of the article or the function of the loop component can be achieved by one of the other components of the article such as the outer cover material.

The important functions intended to be accomplished by the fastening features of absorbent articles have driven the need for aggressive fasteners that can be reliably depended on to secure the articles. Unfortunately, aggressive fastening features can sometimes cause redmarking or irritation of the wearer's skin. The redmarking or skin irritation can occur as a result of a single brushing exposure to the fastening feature or as a result of repeated or constant exposure. A single or limited exposure of the skin to the fastening feature can occur as the article is being applied to the wearer. A repeated or constant exposure of the skin to the fastening feature can occur if the article has been misapplied to the wearer, does not properly fit the wearer or becomes misaligned or mishapen during use of the article. The larger the size and exposure area of the fastening feature, the more likely for skin irritation to occur. Because of the generally occlusive nature of absorbent articles and the irritants from biological wastes with which the occluded skin is inherently brought into contact, irritation of the skin caused by the fastening feature of the article is particularly undesirable. Somehow the needs of "skin friendliness" and secure engagement must be balanced.

There exists a need for a fastening feature that is capable of reliable securement of the various areas of an absorbent article and is capable of not causing irritation or damage to the skin. There also exists a need for a simplified fastening feature that can be used with a prefastened absorbent article and that can reliably maintain the proper relationship between the rear and front waist regions.

SUMMARY OF THE INVENTION

In response to the difficulties and problems discussed above, new prefastened, pant-like disposable absorbent articles that have simplified and improved primary fasteners for forming the prefastened absorbent articles have been invented. As previously described, a common fastening feature for absorbent articles is to provide a hook component and a corresponding loop component for securing the back waist region to the front waist region of the absorbent article. The present invention is directed in part to multiple property fasteners. The multiple property fasteners of the invention provide multiple features such as reliable engagement and skin friendliness (or reduced abrasiveness) in a single fastener.

The present invention is directed to a pant-like, prefastened, disposable absorbent article. The article includes an absorbent, a front waist region, a back waist region and a crotch region that extends between and connects the waist regions. In addition the article includes a longitudinal direction, a lateral direction, an exterior surface and an interior surface opposite the exterior surface. The article also includes a pair of laterally opposed side edges and a pair of longitudinally opposed waist edges. Further the absorbent article includes a multiple property fastener. The multiple property fastener defines a fastener longitudinal direction, a fastener lateral direction and a fastener area. The multiple property fastener further includes at least one engagement zone of a first mechanical fastening material and at least one non-abrasive zone of a second mechanical fastening material. Additionally, the multiple property fastener is oversized to provide stability between the front waist region and the back waist region and to maintain the pant-like, prefastened configuration.

In another aspect of the present invention, the article may include one engagement zone covering one half of the fastener area in the fastener longitudinal direction and one non-abrasive zone covering the other half of the fastener area in the fastener longitudinal direction.

In another aspect of the present invention, the first mechanical fastening material is made from a polypropylene copolymer. Alternatively the second mechanical fastening material is made from a polymer selected from elastomeric thermoplastic polymers and metallocene catalyzed polymers.

In another aspect of the present invention the multiple property fastener is engageable into the front waist region of the article. Alternatively the multiple property fastener is engageable into the back waist region of the article.

In yet another aspect of the present invention the multiple property fastener has a top edge that is generally aligned with one of the waist edges of the article.

It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles and methods of the invention. Together with the description, the drawings serve to explain various aspects of the invention.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

Figure 1:
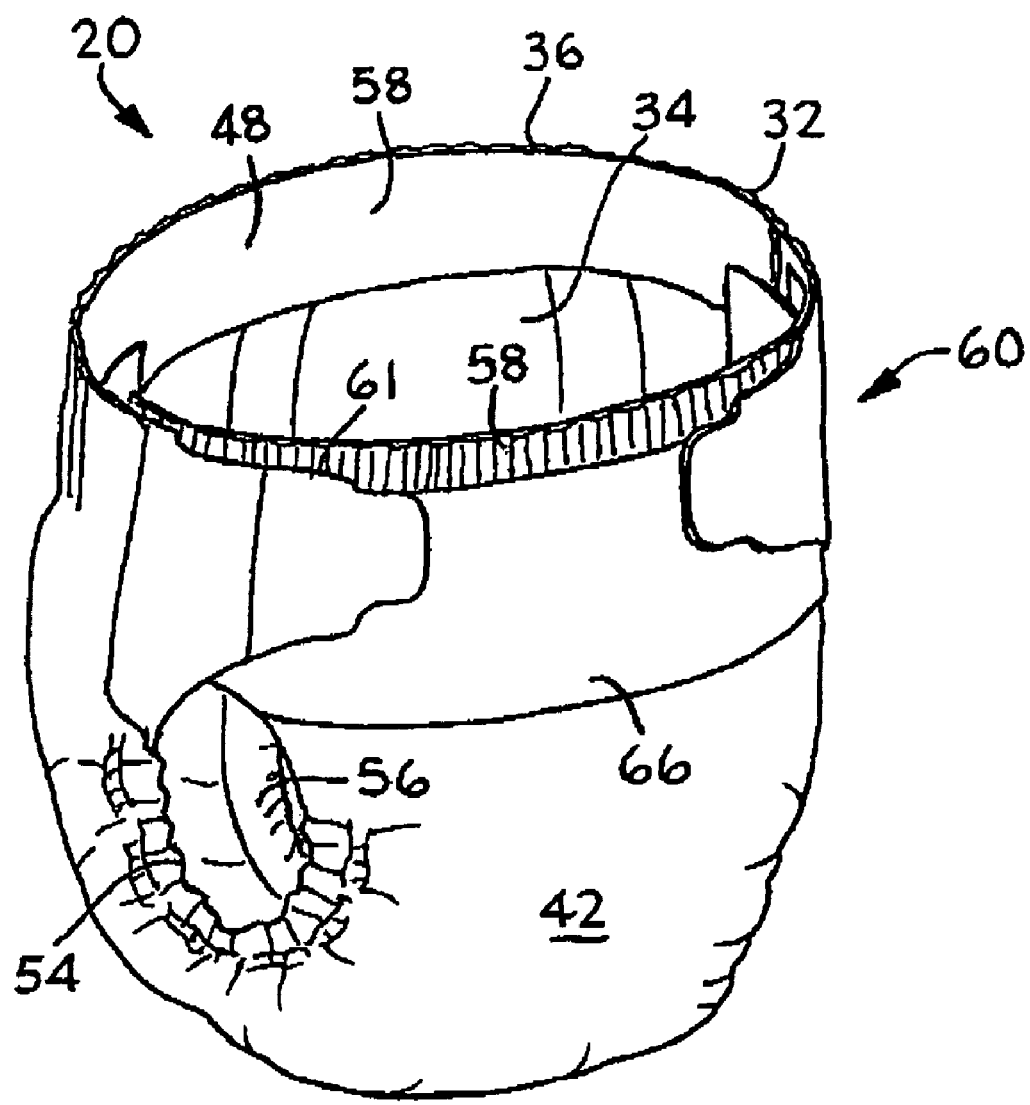
FIG. 1 representatively shows a perspective view of an example of a prefastened absorbent article of the present invention.

The present invention concerns disposable absorbent articles such as pant-like, prefastened articles that are adapted to be worn adjacent to the body of a wearer to absorb and contain various exudates discharged from the body. The prefastened absorbent articles of the invention are configured to closely conform to the body of the wearer to effectively contain body exudates while remaining capable of being pulled up or down over the hips and buttocks of the wearer. The prefastened absorbent articles are also refastenable such that they can be secured to and removed directly from the waist of the wearer and easily inspected to determine if they have been soiled during use. As such, the pant-like, prefastened, disposable absorbent articles of the present invention can function in a similar manner to conventional training pants when left in the prefastened, pant-like configuration, or they can be unfastened prior to or during use to function in a refastenable manner similar to conventional diapers. Moreover, the prefastened absorbent articles include a multiple property fastener that allows the wearer or the caregiver to further improve the fit of the article once it is positioned on the hips of the wearer. As used herein, the term "disposable" refers to articles which are intended to be discarded after a limited use and that are not intended to be laundered or otherwise restored for reuse.

The present invention further relates to solving problems related to the design and manufacturing of prefastened absorbent articles as well as problems associated with conventional fasteners for absorbent articles. Additionally, the present invention relates to reducing the skin irritation potentially associated with exposure of skin to mechanical fasteners.

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The pant-like, prefastened disposable absorbent articles of the present invention will be described in terms of a disposable, pant-like diaper article that is adapted to be worn by infants about the lower torso. In particular, the pant-like disposable absorbent articles will be described in terms of a pant-like, prefastened, disposable diaper having a multiple property fastener. It is understood that the articles of the present invention are equally adaptable for other types of absorbent articles such as adult incontinent products, training pants, feminine hygiene products and other personal care or health care garments.

Figure 1A:
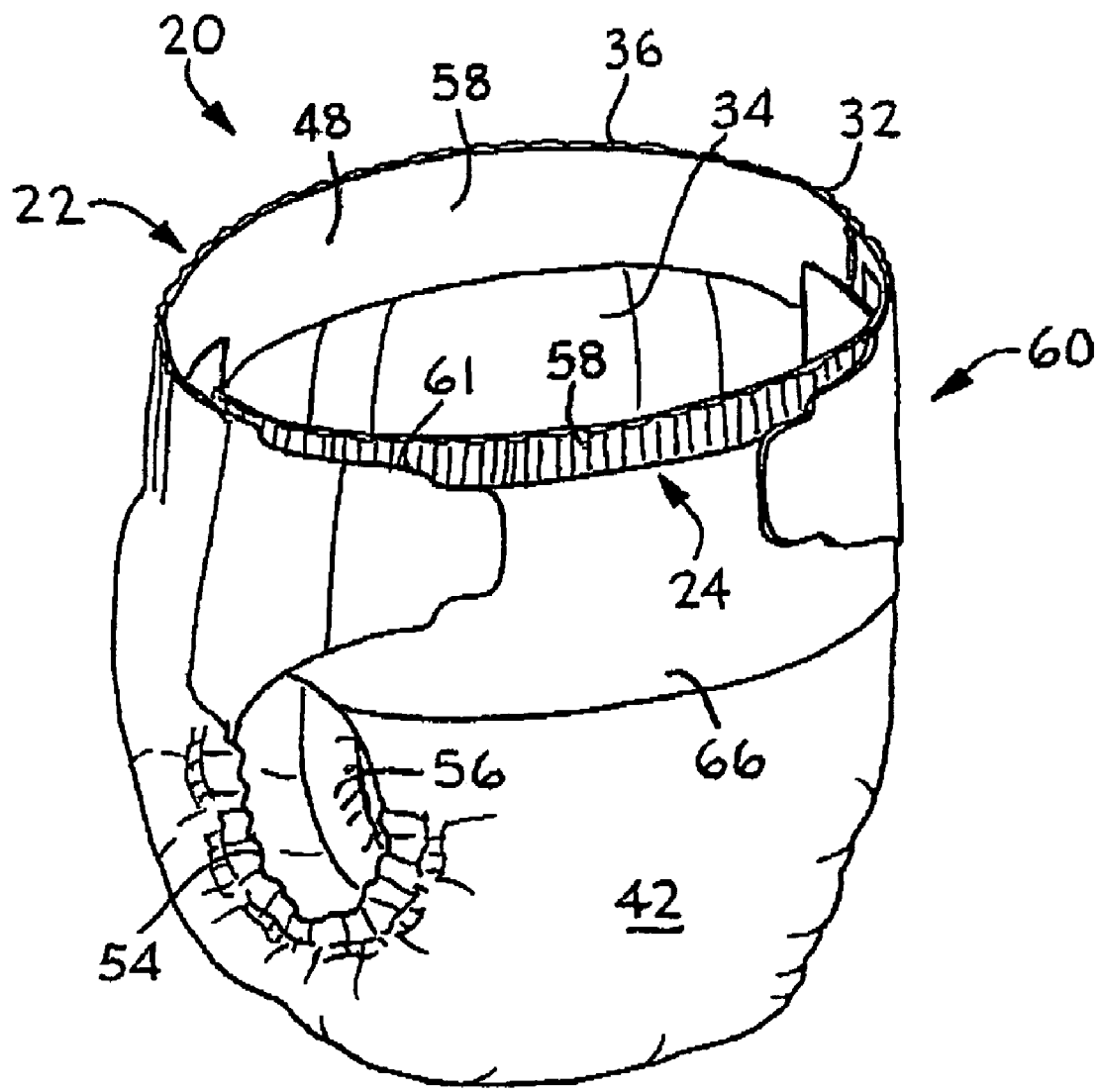
FIG. 1A representatively shows a perspective view of an example of a prefastened absorbent article of the present invention where the fasteners are engagable into the back waist region.
Figure 2:
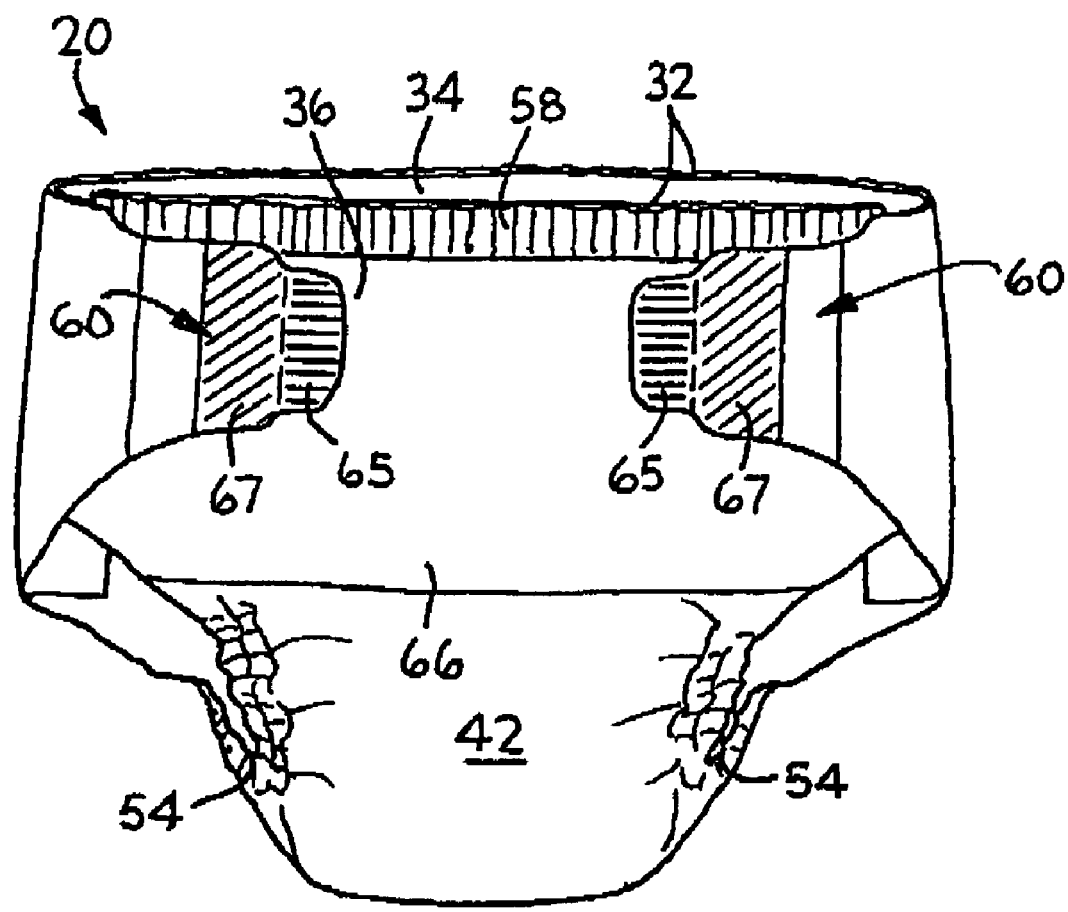
FIG. 2 representatively shows a front plan view of the prefastened absorbent article of FIG. 1.
Figure 3:
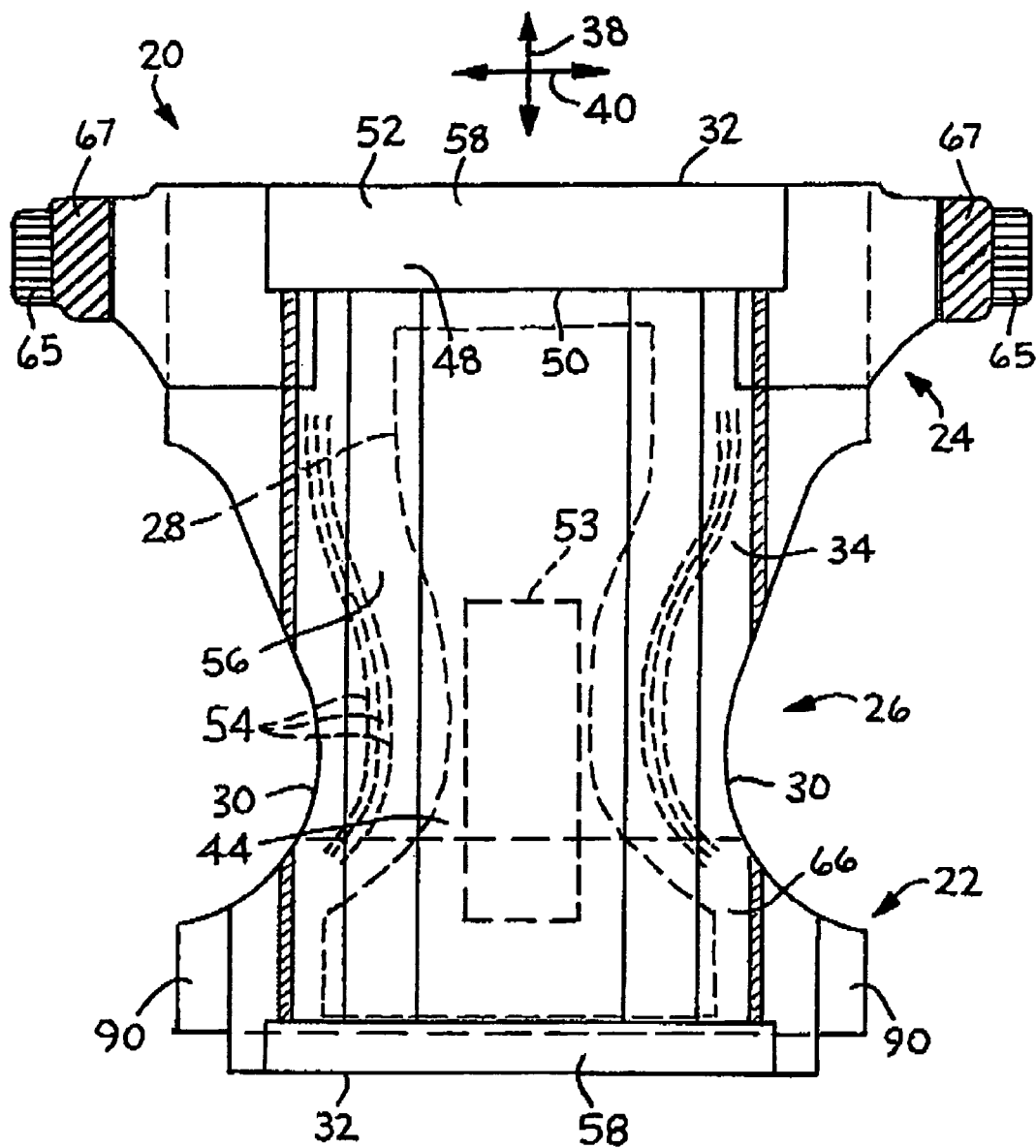
FIG. 3 representatively shows a plan view of the prefastened absorbent article of FIG. 1 in an unfastened, stretched and laid flat condition with the surface of the article which contacts the wearer's skin facing the viewer.
Figure 4:
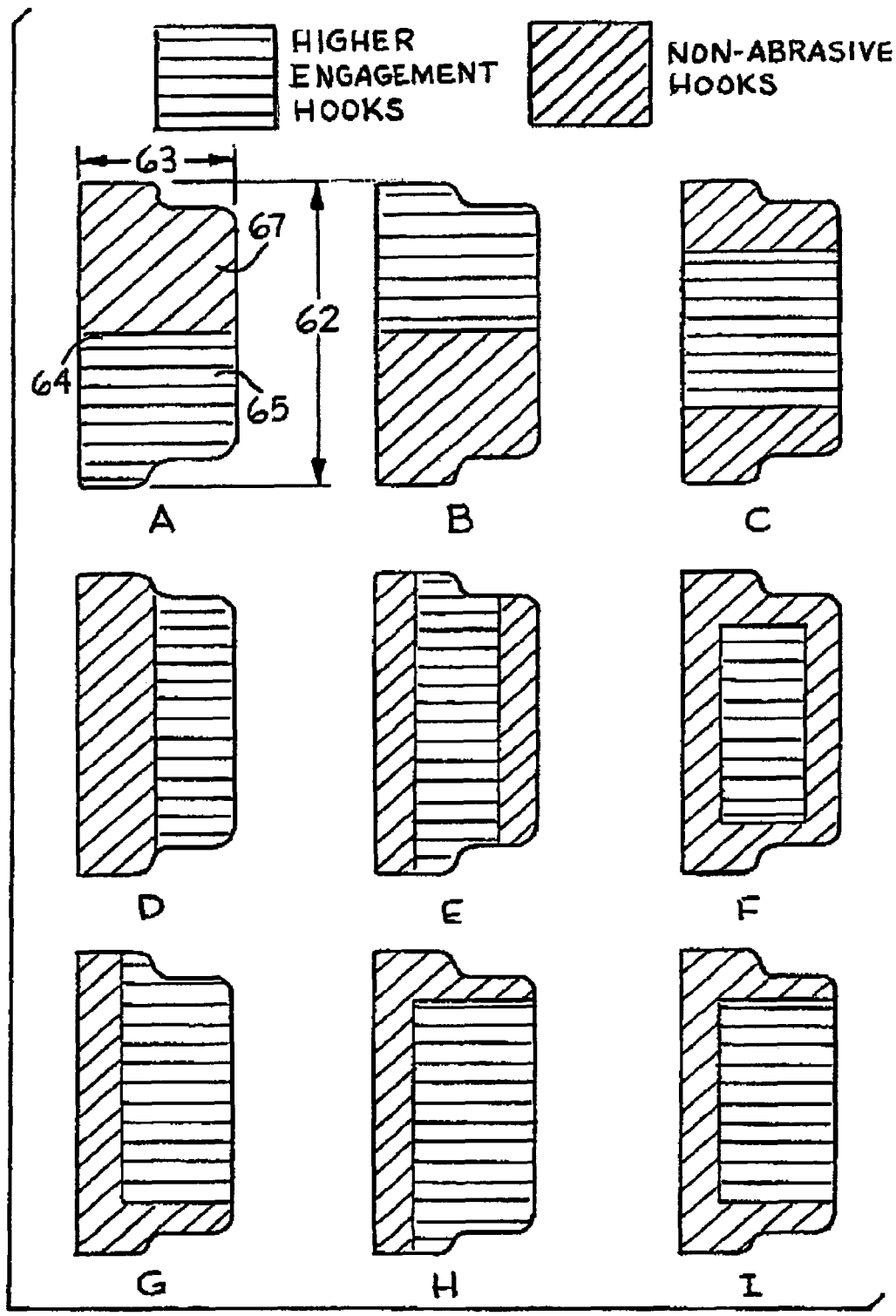
FIGS. 4A-4I representatively show front plan views of various examples of multiple property fasteners that can be used with the prefastened absorbent articles of the invention. The multiple property fasteners can have zones of different hook materials. The multiple property fasteners can also have zones of engagement hooks and non-abrasive hooks in different configurations as depicted in the Figures.

FIG. 1 representatively illustrates an example of a prefastened pant-like, refastenable disposable diaper, as generally indicated at 20, of the present invention. FIG. 1A representatively illustrates an example of a prefastened pant-like, refastenable disposable diaper, as generally indicated at 20, of the present invention where the fasteners are engagable into the back waist region 24. FIG. 2 representatively illustrates a front plan view of the prefastened diaper of FIG. 1. FIG. 3 representatively illustrates a front plan view of the diaper in FIG. 1 wherein one of the continuous fasteners is disengaged and portions of the diaper are partially cut away to show the underlying features. FIG. 4 representatively illustrates the prefastened diaper of FIG. 1 in an unfastened, stretched and laid flat configuration with the surface of the diaper adapted to contact the wearer's skin facing the viewer and with portions of the diaper partially cut away to show the underlying features. As illustrated in FIG. 4, the diaper 20 defines an absorbent 28, a front waist region 22, a back waist region 24, a crotch region 26 that extends between and connects the front and back waist regions 22 and 24, a longitudinal direction 38 and a lateral direction 40. The front waist region 22 includes the portion of the diaper 20 that, when worn, is positioned on the front of the wearer while the back waist region 24 includes the portion of the diaper 20 that, when worn, is positioned on the back of the wearer. The crotch region 26 of the diaper 20 includes the portion of the diaper 20 that, when worn, is positioned between the legs of the wearer and covers the lower torso of the wearer.

The diaper 20 defines a pair of laterally opposed side edges 30, a pair of longitudinally opposed waist edges 32, an interior surface 34 that is configured to contact the wearer, and an exterior surface 36 opposite the interior surface 34 that is configured to contact the wearer's clothing in use. The illustrated diaper 20 also includes an outer cover 42 and a bodyside liner 44 that is connected to the outer cover 42 in a superposed relation. An absorbent 28 is located between the outer cover 42 and the bodyside liner 44. The laterally opposed side edges 30 of the diaper 20 are generally defined by the side edges of the outer cover 42 that further define leg openings that may be curvilinear. The waist edges 32 of the diaper 20 are generally defined by the waist edges of the outer cover 42 and define a waist opening that is configured to encircle the waist of the wearer when worn. The absorbent 28 is configured to contain and/or absorb any body exudates discharged from the wearer. The diaper 20 may further include leg elastics 54, containment flaps 56 and waist elastics 58 as are known to those skilled in the art. It should be recognized that individual components of the diaper 20 may be optional depending upon the intended use of the diaper 20.

The diaper 20 further includes refastenable, prefastened multiple property fasteners 60. The multiple property fasteners 60 releasably engage the opposed side edges 30 of the diaper 20 in the opposite waist regions. The multiple property fasteners 60 define a fastener longitudinal direction 62, a fastener lateral direction 63 and a fastener area 64 (as shown in FIG. 4). The multiple property fasteners 60 include at least one engagement zone 65 of a first mechanical material and at least one non-abrasive zone 67 of a second mechanical fastening material. The multiple property fasteners 60 can be "oversized" to provide stability between the front waist region 22 and the back waist region 24 and to maintain a pant-like, prefastened configuration. The multiple property fasteners 60 have a top edge 61 that can be generally aligned with one of the waist edges 32 of the prefastened article 20. Further, the prefastened article 20 may include an attachment panel 66 located on the front or back waist region 22 and 24, opposite the multiple property fasteners 60 to which the fasteners 60 are releasably engaged to form the prefastened article 20.

The diaper 20 may be of various suitable shapes. For example, in the unfastened configuration as illustrated in FIG. 3, the diaper may have an overall rectangular shape, T-shape or an approximately hourglass shape. In the shown embodiment, the diaper 20 has a generally I-shape in an unfastened configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic bonds, thermal bonds or the like, as well as combinations thereof. In the shown embodiment, for example, the outer cover 42 and bodyside liner 44 are assembled to each other and to the absorbent 28 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent 28 may be connected to the outer cover 42 using conventional fasteners such as buttons, hook and loop type fasteners, adhesive tape fasteners, and the like. The other components of the diaper 20 may be suitably connected together using similar means. Similarly, other diaper components, such as the elastic members 54 and 58 and the multiple property fasteners 60, may be assembled into the diaper 20 article by employing the above-identified attachment mechanisms. Desirably, the majority of the diaper components are assembled together using ultrasonic bonding techniques for reduced manufacturing cost.

The outer cover 42 of the diaper 20, as representatively illustrated in FIGS. 1-3, may suitably be composed of a material which is either liquid permeable or liquid impermeable. It is generally preferred that the outer cover 42 be formed from a material that is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). If it is desired to present the outer cover 42 with a more clothlike feeling, the outer cover 42 may be formed from a polyolefin film having a nonwoven web laminated to the exterior surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers. The polypropylene fibers have a thickness of about 1.5 to 2.5 denier per filament, which nonwoven web has a basis weight of about 17 grams per square meter (0.5 ounce per square yard). The outer cover 42 may otherwise include bicomponent fibers such as polyethylene/polypropylene bicomponent fibers. Methods of forming such clothlike outer covers are known to those skilled in the art. The outer cover 42 may also be an extensible outer cover such as the outer covers described in U.S. patent application Ser. No. 09/563,417 filed on May 3, 2000 by Roessler et al. The disclosure of application Ser. No. 09/563,417 is intended to be incorporated herein to the extent it is consistent with the present disclosure.

Further, the outer cover 42 may be formed of a woven or nonwoven fibrous web layer which has been totally or partially constructed or treated to impart a desired level of liquid impermeability to selected regions that are adjacent or proximate the absorbent 28. Still further, the outer cover 42 may optionally be composed of a micro-porous "breathable" material which permits vapors to escape from the absorbent 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued to McCormack et al. and U.S. Pat. No. 5,843,056 issued Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. The outer cover 42 can also be embossed or otherwise provided with a matte finish to provide a more aesthetically pleasing appearance.

The bodyside liner 44, as representatively illustrated in FIG. 3, suitably presents a bodyfacing surface that is compliant, soft feeling, and nonirritating to the wearer's skin. Further, the bodyside liner 44 may be less hydrophilic than the absorbent 28, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent 28. The bodyside liner 44 can also be made from extensible materials as are described in U.S. patent application Ser. No. 09/563,417 filed on May 3, 2000 by Roessler et al.

Various woven and nonwoven fabrics can be used for the bodyside liner 44. For example, the bodyside liner may be composed of a meltblown or spunbond web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In a particular embodiment of the present invention, the bodyside liner 44 is made from a nonwoven, spunbond, polypropylene fabric composed of about 2.8-3.2 denier fibers formed into a web having a basis weight of about 20 grams per square meter and a density of about 0.13 grams per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or similar techniques. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto that is configured to be transferred to the wearer's skin. Suitable compositions for application to the bodyside liner 44 are described in U.S. Pat. No. 6,149,934 that issued to Krzysik et al. on Nov. 21, 2000.

The absorbent 28 of the diaper 20, as representatively illustrated in FIG. 3, may suitably be composed of a matrix of hydrophilic fibers, such as a web of cellulosic fluff, mixed with particles of a high-absorbency material commonly known as superabsorbent material. In a particular embodiment, the absorbent 28 includes a matrix of cellulosic fluff such as wood pulp fluff and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent 28 to better contain and absorb body exudates. The concentration of the superabsorbent particles may also vary through the thickness of the absorbent 28. Alternatively, the absorbent 28 may include a laminate of fibrous webs and superabsorbent material or other suitable means of maintaining a superabsorbent material in a localized area.

The absorbent 28 may have any of a number of shapes. For example, the absorbent may be rectangular, I-shaped, or T-shaped. It is generally preferred that the absorbent 28 be narrow in the crotch region 26 of the diaper 20. It has been found that the absorbent 28 of the present invention is particularly useful when the width dimension in the crotch region 26 is from about 2.5 to about 12.7 centimeters (1.0 to about 5.0 inches), desirably no more than about 7.6 centimeters (3.0 inches) and more desirably no more than about 5.1 centimeters (2.0 inches). The narrow crotch width dimension of the absorbent 28 allows the absorbent 28 to better fit between the legs of the wearer. The size and the absorbent capacity of the absorbent 28 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and similar compounds. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Virginia and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent 28.

Optionally, a substantially hydrophilic tissue wrapsheet may be employed to help maintain the integrity of the airlaid fibrous structure of the absorbent 28. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer that helps to rapidly distribute liquid over the mass of absorbent fibers comprising the absorbent body. The wrapsheet material on one side of the absorbent fibrous mass may be bonded to the wrapsheet located on the opposite side of the fibrous mass to effectively entrap the absorbent 28. There may also be a surge layer 53 located between the absorbent body 28 and the bodyside liner 44 to facilitate the distribution of fluid during intake.

As representatively illustrated in FIGS. 1 and 3, the disposable diaper 20 may include a pair of containment flaps 56 that are configured to provide a barrier to the lateral flow of body exudates. The containment flaps 56 may be located along the laterally opposed side edges 30 of the diaper adjacent the side edges of the absorbent 28. Each containment flap 56 typically defines an unattached edge that is configured to maintain an upright, perpendicular configuration in at least the crotch region 26 of the diaper 20 to form a seal against the wearer's body. The containment flaps 56 may extend longitudinally along the entire length of the absorbent 28 or may only extend partially along the length of the absorbent 28. When the containment flaps 56 are shorter in length than the absorbent 28, the containment flaps 56 can be selectively positioned anywhere along the side edges 30 of diaper 20 in the crotch region 26. In a particular aspect of the invention, the containment flaps 56 extend along the entire length of the absorbent 28 to better contain the body exudates.

Such containment flaps 56 are generally well known to those skilled in the art. For example, suitable constructions and arrangements for containment flaps 56 are described in U.S. Pat. No. 4,704,96 issued Nov. 3, 1987, to K. Enloe, the disclosure of which is hereby incorporated by reference.

The diaper 20 of the different aspects of the present invention may further include elastics at the waist edges 32 and side edges 30 of the diaper 20 to further prevent leakage of body exudates and support the absorbent 28. For example, as representatively illustrated in FIGS. 1-3, the of the present invention may include a pair of leg elastic members 54 that are connected to the laterally opposed side edges 30 of the diaper 20 in the crotch region 26. The diaper 20 may also include a pair of waist elastic members 58 that is connected to the longitudinally opposed waist edges 32 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material that are adhered to the outer cover 42 in a stretched position, or that are attached to the outer cover 42 while the outer cover is pleated, such that elastic constrictive forces are imparted to the outer cover 42. The leg elastics 54 may also include such materials as polyurethane, synthetic and natural rubber.

The diaper 20 of the different aspects of the present invention may further include a fit panel 48 superimposed adjacent to the waist edge 30 in at least one of the waist sections 22 and 24, to provide a more comfortable, contouring fit about the wearer. For example, as illustrated in FIG. 3, the may include a fit panel 48 superimposed adjacent the waist edge 32 on either the interior or exterior surface 34 and 36 of the diaper 20. Or there may be a fit panel located on both surfaces 34 and 36 of the diaper 20 simultaneously. The diaper may include a fit panel disposed in both waist sections 22 and 24 and desirably the diaper includes a fit panel in at least the rear waist section 24. Desirably, the fit panel is extensible or elastomeric. For example, as representatively illustrated in FIG. 3, the diaper 20 includes an elastomeric fit panel 48 on the interior surface 34 of the diaper 20 that is configured to elongate in the lateral direction 40 to provide an improved fit and appearance of the absorbent article about the wearer. This is accomplished by providing a mechanism for the waist region to expand, thereby increasing the waist perimeter dimension to assist in applying the diaper 20 on the wearer. Desirably the elastomeric or extensible fit panel 48 allows the waist perimeter dimension to expand at least about 20 percent, more desirably at least about 40 percent and even more desirably at least about 50 percent. The fit panel 48 is further capable of initially providing a conforming fit about the wearer and maintaining such fit throughout the use of such article. The fit panel 48 is also configured such that the absorbent 28 has the ability to expand, contract and receive body exudates without adversely affecting the positioning of the fit panel 48 and the article about the waist of the wearer. Thus, with such a fit panel 48, movements of the wearer may move the absorbent but do not adversely affect the overall positioning and fit of the article on the wearer. Such improved fit can result in reduced leakage from the absorbent article and a more aesthetically pleasing appearance. As representatively illustrated in FIG. 3, when the fit panel 48 is located on the interior surface 34 it may also extend beyond the side edges of the absorbent 28 of the diaper 20 and be generally coterminous with the waist edge 32 of the diaper 20 in the respective waist section 22 or 24. When located on the interior surface 34 of the diaper 20, the fit panel 48 may define a free edge 50 that extends longitudinally inward towards the crotch region 26 of the diaper 20. In a particular embodiment the free edge 50 of the fit panel 48 is configured to remain at least partially unattached to the of the diaper 20 when in use to allow the absorbent 28 to move and expand to receive and contain body exudates. The unattached free edge 50 may also form a pocket between the fit panel 48 and the bodyside liner 44 that is configured to further contain body exudates. The free edge 50 of the fit panel 48 may be linear or curvilinear, such as concave, to better fit the wearer. The waist edge 52 of the fit panel 48 may also be curvilinear to better fit the wearer. Desirably, if the free edge 50 is curvilinear, the waist edge 52 is also curvilinear such that consecutive fit panels 48 for multiple articles nest within each other and can be provided from a continuous sheet of material. In such a configuration, the free edge 50 of the first fit panel corresponds to the waist edge 52 of the next fit panel to improve manufacturing and reduce waste.

The fit panel 48 as representatively illustrated in FIG. 3 can be provided in any suitable manner that provides the desired fit properties and performance. Desirably, the fit panel 48 is an elastomeric or extensible material. The materials may include a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220, issued May 5, 1987 to T. Wisneski et al., the disclosure of which has previously been incorporated by reference. Examples of composite fabrics comprising at least one layer of a nonwoven material secured to a fibrous elastic layer are described in European Patent Application No. EP 090 010 published on Apr. 8, 1987 with the inventors listed as J. Taylor et al., the disclosure of which has previously been incorporated by reference. Examples of NBL materials are described in U.S. Pat. No. 5,226,992 issued Jul. 13, 1993 to Mormon, the disclosure of which has previously been incorporated by reference.

Alternatively, the fit panel 48 may be provided by a substantially non-elastomeric material, such as polymer films, woven fabrics, non-woven fabrics, or similar materials such as described above as being suitable for the outer cover 42 or the bodyside liner 44. For example, the fit panel 48 may include a polyethylene film having a nonwoven web laminated to the outer surface thereof. The fit panel 48 may also be formed of a woven or nonwoven fibrous web layer that has been totally or partially constructed or treated to impart a desired level of liquid impermeability, or wettability and hydrophilicity. Still further, the fit panel 48 may optionally be composed of a micro-porous "breathable" material that permits vapors to escape from between the fit panel 48 and the bodyside liner 44 of the diaper 20.

The fit panel 48 of the different embodiments of the present invention may be attached to the diaper 20 in any suitable manner that provides the desired properties. For example, the fit panel 48 may be attached to the diaper using adhesive, ultrasonic, thermal bonding techniques and the like or combinations thereof. Absorbent articles including such a fit panel 48 and methods of making the same are further described in PCT Patent Application WO 97/48357 published Dec. 24, 1997 and entitled "ABSORBENT ARTICLE HAVING FIT PANEL", the disclosure of which is hereby incorporated by reference.

The diaper 20 of the different aspects of the present invention can further include a pair of multiple-property fasteners 60 that can be used to form a prefastened article and that can act as a waist size adjustment means for reducing or increasing the waist perimeter dimension after the diaper has been pulled on over the hips of the wearer. In such a configuration, the prefastened diaper 20 can be pulled on or off over the legs and hips of the wearer. If the prefastened diaper 20 becomes soiled during use, the multiple property fasteners 60 can be disengaged to easily remove diaper 20 the from the waist of the wearer with reduced risk of undesirably soiling the clothes or legs of the wearer. The multiple property fasteners 60 can also be easily disengaged to inspect the diaper 20 for possible soiling or to first apply the diaper to the wearer if desired. Thus, the diaper 20 is configured to be pulled on or off over the hips of the wearer similar to conventional training pants and can be readily applied or removed by disengaging the multiple property fasteners 60 similar to conventional diaper articles.

In the illustrated embodiments, the fasteners 60 are permanently attached directly to the side edges 30 of the diaper 20 in one of the waist regions 22 and 24. The fasteners 60 may be permanently adhered to the side edges 30 of the diaper 20 by any means known to those skilled in the art such as adhesive bonds, sonic bonds or thermal bonds. Desirably, the fasteners 60 are permanently attached to the back waist region 24 in which there is an extensible fit panel 48. Alternatively, the fasteners 60 may be permanently attached to the extensible fit panel 48. Attaching the fasteners 60 onto the same waist region 22 and 24 as the extensible fit panel 48, or directly to the extensible fit panel 48, provides added fit, flexibility, and an optimum seal in the waist regions 22 and 24 once the is positioned on the wearer. If the fasteners 60 are not attached directly to the extensible fit panel 48, that can be attached to an area or segment in the waist region that is also extensible or elastomeric.

An attachment panel 66 may be located on the outer cover 42 to which the multiple property fasteners 60 are releasably engaged. As representatively illustrated in FIG. 1, the disposable diaper 20 of the present invention may include an attachment panel 66 located on the outer cover 42 in one of the waist regions 22 and 24 on the exterior surface 36 of the diaper 20. In such a configuration, the multiple property fasteners 60 are refastenably engaged with the attachment panel 66 to maintain the diaper 20 about the waist of the wearer. The attachment panel 66 may include two separate panels located along the opposed side edges of the diaper 20 in one of the waist regions 22 and 24 of the diaper 20. Alternatively, the attachment panel 66 may include a single piece of material that extends substantially across the respective waist region of the diaper 20. In this configuration, the attachment panel 66 located on the outer cover 42 may further extend beyond the side edges 30 of the diaper 20 to form front ear portions 90 as depicted in FIG. 3. The attachment panel material can be shaped into the front ear portions 90 using any one of several known techniques including water and die cutting. Front ear portions 90 provide several benefits including easier positioning of the diaper on the wearer. Advantages of forming the front ear portions 90 from the attachment panel 66 include ease of manufacturing and reduction in the number of components.

Suitable fastening materials to provide the engageable portions of the multiple property fasteners 60 are well known to those skilled in the art and can include adhesive tape tab fasteners, hook and loop fasteners, mushroom fasteners, snaps, pins, belts and the like, and combinations thereof. The multiple property fasteners 60 may include hook type fasteners and the outer cover 42 may be configured to function as a complementary loop type fastener. Alternatively, attachment panel 66 may be provided on the diaper 20 to function as a complementary loop type fastener. Desirably, the multiple property fasteners 60 are hook type fasteners that are releasably engageable directly with the outer cover 42 of the diaper 20. Such an arrangement provides the ability to vary the size of the waist opening in very small increments over a wide range to fit the waist of the wearer.

The multiple property fastener 60 of the present invention may also include a fastener substrate to which the continuous fastener 60 is attached. The fastener substrate may be advantageously made of different materials. For example, the fastener substrate may consist of an extensible or elastomeric panel. In such configurations, the substrate of the continuous fastener 60 provides improved fit and comfort to the wearer by allowing the continuous fastener 60 more flexibility and range in engaging the exterior surface 36 of the diaper 20. The fastener substrate may be made of material well known in the art. The materials may include a stretch-bonded-laminate (SBL) material, a neck-bonded-laminate (NBL) material, an elastomeric film, an elastomeric foam material, or the like such as described above as being suitable for the fit panel 48. The fastener substrate may alternately be provided by a substantially non-elastomeric material, such as polymer films, woven fabrics, non-woven fabrics, or similar materials such as described above as being suitable for the outer cover 42 or the bodyside liner 44.

The multiple property fastener 60 of the invention defines a fastener longitudinal direction 62, a fastener lateral direction 63 and a fastener area 64. The multiple property fastener also includes one or more engagement zones 65 of a first mechanical fastening material and one or more non-abrasive zones 67 of a second mechanical fastening material. The multiple property fastener 60 can be oversized so that the diaper 20 can be provided in a pant-like, prefastened configuration. The "oversizing" of the multiple property fastener 60 contributes to the fastener 60 providing stability between the front waist region 22 and the back waist region 24. The engagement zones 65 of the multiple property fastener 60 can have a primary function of providing secure and reliable engagement into a loop material or other material or surface desired for engagement. The non-abrasive zones 67 can have a primary function of providing engagement while being "skin-friendly" or less likely to cause irritation of the skin with which these zones come into contact. The zones of the multiple property fastener 60 of the invention can be configured to provide a fastener having a gradient of properties across the longitudinal direction 62 or lateral direction 63 of the fastener.

The first mechanical fastening material of the engagement zones 65 is desirably selected to provide strong engagement with another surface. When the mechanical fastening material is a hook-type material, it is desirable to select a hook that provides strong engagement with a loop-type material. Types of hook materials that provide suitable engagement for use on absorbent articles are known. One feature of hook materials that correlates to their engagement properties is the density of the hook material. Suitable hook materials generally have from about 100 to about 4000 hooks per square inch (about 16 to about 620 hooks per square centimeter). Alternatively, the hook material has a density of from about 800 to about 2500 hooks per square inch (about 124 to about 388 hooks per square centimeter); more particularly, the hook material has a density of from about 1000 to about 2000 hooks per square inch (about 155 to about 310 hooks per square centimeter). Another feature of the hook material affecting strength of engagement is the height of the hooks of the hook material. Hooks acting as the first mechanical fastening material of the multiple property fasteners 60 of the invention suitably have a height of from about 0.001 inches (0.00254 centimeters) to about 0.201 inches (0.51 centimeters). Alternatively, the hooks have a height of from about 0.015 inches (0.0381 centimeters) to about 0.03 inches (0.0762 centimeters).

Hook density (number of hooks per square centimeter) is another parameter that affects the strength with which a fastening material engages. Hook material can be fabricated to have a hook density of from about 60 hooks/cm² to about 1600 hooks/cm². More particularly, the hook material can have a hook density of from about 100 hooks/cm² to about 750 hooks/cm². The term "hook"—as used in relation to the first mechanical fastening material as well as the second mechanical fastening material of the invention—should be understood to encompass various geometries of protuberances that are suitable for engaging into a loop material or a material having loop characteristics in order to place or secure a fastener. Exemplary geometries include prongs, stems, trees (such as the shapes connoted by "evergreen" and "palm" trees), mushrooms, J-hooks, bi-directional hooks and studs protruding at various angles. In addition to the various possible geometries of hooks, the hooks may protrude from a backing material at various angles. Additionally, U.S. Pat. No. No. 5,782,8199 issued to Tanzer et al. on Jul. 21, 1998 describes a fastener system that includes velvet fabrics as examples of materials exhibiting differential friction. The surface of velvet fabric has fibers protruding from the surface, oriented on a bias. Despite the fibers being essentially straight (i.e. without barbs or hooks), they engage an opposed surface and facilitate fastening. Such fibers can be used to form the first and second mechanical fastening materials of the invention.

Another property affecting the "engageability" of a hook material is the relative coefficient of friction. The discrete hooks of the hook material may include or be treated with materials such as soft rubbers that increase the coefficient of friction of the hooks against the corresponding loop/engaging material. The increased coefficient of friction serves to reduce the tendency of the fastener to pop-open under stress. The benefits of fasteners having increased coefficients of friction are described in U.S. patent application Ser. No. 09/705,512 entitled "Hook and Loop Fastener Having an Increased Coefficient of Friction" filed by Martin et al. on Nov. 3, 2000.

Particular examples of a first mechanical fastening material can include VELCRO HTH 858 or VELCRO HTH 823, or a similar hook material available from Velcro Industries B. V., Amsterdam, Netherlands or affiliates thereof.

Hook materials are typically produced using a process of continuous injection molding of a polymeric material, such as a polypropylene copolymer. Desirably, the polymeric material for the first mechanical fastening material is selected to have a flexural modulus greater than about 30 kilopounds per square inch (kpsi). More particularly, it is suitable for the hook material to have a flexural modulus of from about 50 kpsi to about 300 kpsi and, alternatively, of from about 150 kpsi to about 250 kpsi. Comparatively, the polymeric material for the second mechanical fastening material (used in the non-abrasive zones 67) is selected to have a bulk flexural modulus in a range of about 7 kpsi (48 MPa) to about 30 kpsi (207 MPa), preferably about 7 kpsi (48 MPa) to about 25 kpsi (173 MPa), and more preferably about 7 kpsi (48 MPa) to about 15 kpsi (104 MPa).

The second mechanical fastening material of the multiple property fastener 60 of the invention is intended to be less abrasive and more skin-friendly, that is, less likely to cause irritation when brought into contact with the skin. In order to provide the property of being less abrasive and more skin friendly, the second mechanical fastening material can be selected to have various properties and combinations of properties. Examples of suitable mechanical fastening materials are described in U.S. patent application Ser. No. 09/793,057 filed on Feb. 26, 2001 and titled "SKIN-FRIENDLY HOOK FASTENING COMPONENT".

One such property is the "aspect ratio" of the fastening material. The "aspect ratio" refers to the relative hook head density of a hook component. This ratio is related to the area of the engaging head of a hook that corresponds with the maximum instantaneous displaced area of a mating loop component as the hook head penetrates the loop component. In the context of the invention, it affects the feel of the hook component as the hook heads come into contact with a person's skin. The aspect ratio is measured as the aggregate hook head area divided by the overall area of the hook component. The hook head area is measured at an elevation above the hook backing that includes the maximum overhang of the hook head. In order to provide a non-abrasive fastening material, the hook component of the fastening material desirably has an overall aspect ratio, as defined herein, within a range of 40 to 55 percent.

Figure 5A:
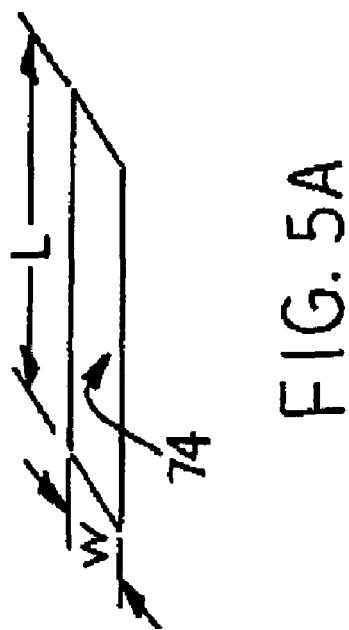
FIG. 5A is a supporting diagram to illustrate the method by which hook head area is calculated.
Figure 5:
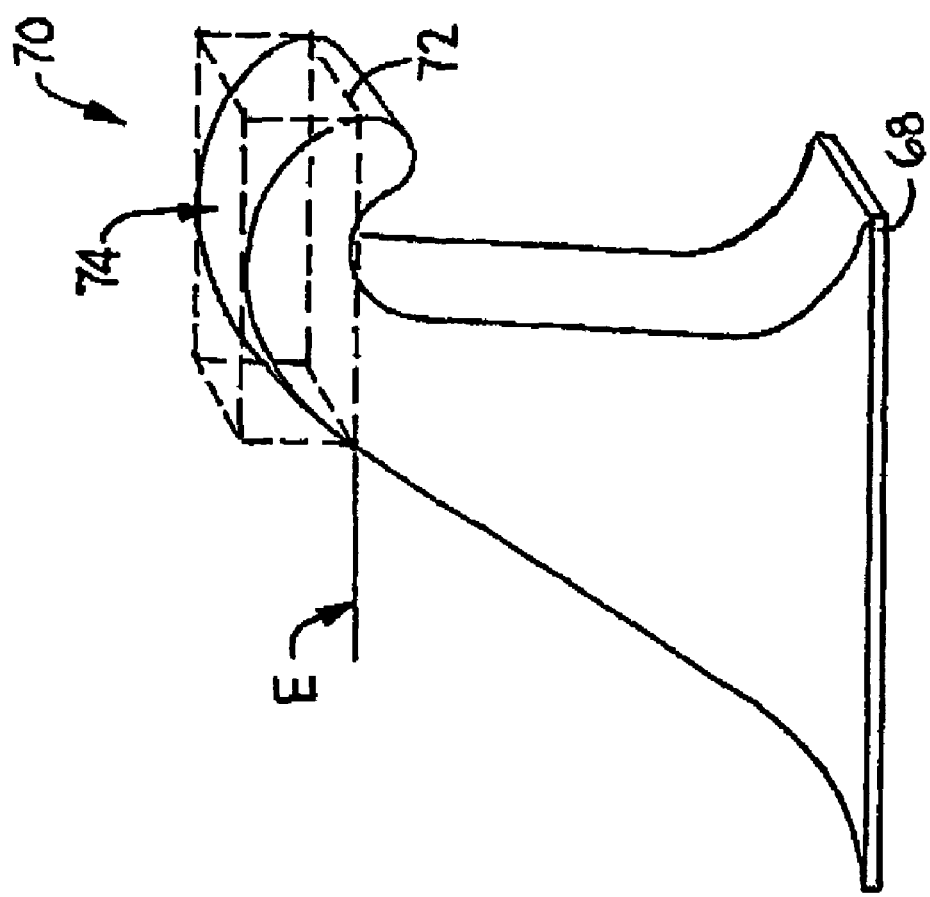
FIG. 5 representatively shows a perspective view of an individual hook of a hook fastening material and the dimensions by which the aspect ratio of the hook can be determined.

FIGS. 5 and 5A illustrate how the hook head area is determined for calculating the aspect ratio of a hook component. The head area is calculated at an elevation "E" corresponding to the maximum lateral overhang of the hook head at 72, as the area of the upper face 74 of the smallest parallelepiped (shown in dashed outline) having its base at "E" and parallel to fastener backing 68, its front face intersecting maximum overhang point 72, and completely containing the portion of the hook head above elevation "E". As shown in FIG. 5A, the hook head area is the product of perpendicular dimensions "W" and "L". An individual hook 70 having a large head area in contact with a wearer's skin is more skin-friendly than an individual hook 70 having a small head area, such as a pointed end, in contact with a wearer's skin.

Another property of the second mechanical fastening material that makes it non-abrasive is to provide the fastening material with a hook component that includes a polymer selected from elastomeric thermoplastic polymers and metallocene catalyzed polymers. Suitable elastomeric thermoplastic polymers can be made from block copolymers such as polyurethanes, copolyether esters, polyamide polyether block copolymers, polyester block amide copolymers, ethylene vinyl acetates (EVA) and block copolymers having the general formula A-B-A' or A-B. Polypropylene, polyethylene and polyurethane are other useful elastomeric materials.

The density of the hook component in the second mechanical fastening material is another property that can be adjusted to provide non-abrasiveness. Desirably, the hooks are arranged on the hook backing, in some embodiments, in a density of 155 to 310 hooks per square centimeter. The shape of the hook component can also be modified to reduce abrasiveness. For example, the hooks of the hook component can be J-shaped and/or have heads of molded resin and/or have at least one flat lateral side. Another mode by which to achieve non-abrasiveness is for the hook component to include a hook backing with non-uniform thickness such that there are areas of greater thickness about the hooks and areas of lesser thickness between the hooks.

In another aspect, the second mechanical fastening material can incorporate a hook component with tapered edges about a periphery of the hook backing. With respect to the thickness of the hook component, the hook backing can have a thickness in a range from a positive amount to 3.5 mils (88.9 microns). Further, the hook backing may be provided with a knurled texture on at least one surface, or apertures therethrough, for improved flexibility. Such improved flexibility can reduce the abrasiveness of the second mechanical fastening material. In another approach to reducing the abrasiveness of the fastening material, a plurality of the hooks of the hook component can each have at least one rounded free end, and each of the hooks can be formed from a polymer having a bulk flexural modulus in a range of 7 kpsi (48 MPa) to 30 kpsi (207 Mpa). With respect to the material used to form the backing of the hook component, the hook backing can be formed from a polymer having a bulk flexural modulus in a range of 7 kpsi (48 MPa).

In order to optimize the non-abrasiveness of the second mechanical fastening material, the hook component can usefully include more than one of these physical features for improved skin-friendliness. In one such combination, the hook component has an overall aspect ratio within a range of 40 to 55 percent, the hook backing has a non-uniform thickness with areas of greater thickness about the hooks and areas of lesser thickness between the hooks, and each of the hooks comprises a polymer having a bulk flexural modulus in a range of 7 kpsi (48 MPa) to 30 kpsi (207 Mpa).

As part of selecting first and second mechanical fastening materials for the engagement and non-abrasive zones 65 and 67 of a fastener, it is desirable to maintain the overall flexibility of the fastener. One known parameter for measuring the flexibility or relative stiffness of a fastener is the Gurley stiffness value; it is desirable for the fastener to have a Gurley stiffness value of less than about 1000 milligrams. Alternatively, the multiple property fastener of the invention has a Gurley stiffness value of less than about 500 milligrams, alternatively of less than about 200 milligrams or alternatively of less than about 75 milligrams. A suitable technique for determining Gurley stiffness values is set forth in TAPPI Standard Test T 543 om-94 (Stiffness of paper (Gurley type stiffness tester)). When a mechanical fastening material has a relatively high flexural modulus, the overall fastener tends to have a relatively high Gurley stiffness value. Therefore, when the polymeric material from which the mechanical fastening material is formed has a relatively high flexural modulus, it is desirable to alter other aspects of the fastener to lower the Gurley stiffness. For example, the base sheet material of the mechanical fastener material can be selected to be thinner. For example, the base sheet material may have a thickness of from about 0.001 inches to about 0.020 inches (about 0.00254 centimeters to about 0.0508 centimeters), alternatively of from about 0.002 inches to about 0.015 inches (about 0.00508 centimeters to about 0.0381 centimeters). Other aspects of the mechanical fastening material that can be altered include hook orientation (when the fastening material is of a "hook" type), spacing, backing thickness, hook thickness and the shape (or configuration) of the fastening material.

The multiple property fasteners 60 of the invention are capable of reducing the incidence of skin irritation without compromising the performance of the fastener. In order to reduce the incidence of skin irritation, the non-abrasive zone (s) 67 of the fastener is located in the areas of the fastener that are most likely to come into contact with the skin of the wearer or caregiver. The various zones of engagement and non-abrasiveness 65 and 67 within the multiple property fastener 60 can be achieved using manufacturing techniques and different materials. Different materials can be combined during manufacture of the hook component to form rows of hooks having different properties. Rows of hook component in the multiple property fastener 60 can be formed in the longitudinal and lateral directions in such a way that each row has a different property with respect to engagement and non-abrasiveness. Rows of hooks can be formed in such a way that each row has an increased degree of engageability over the row formed before it. In some cases, the increased engageability is achieved by forming hooks with increasing stiffness. In some cases, reduced abrasiveness is achieved by forming hooks with decreased stiffness. When stiffness is the distinguishing criterion between engageability and non-abrasiveness, the stiffness gradient can be formed so that the most flexible hooks are located in the portion(s) or zones of the fastener most likely to come into contact with the skin. In addition to actually forming the hooks to have different properties along adjacent rows, the hook component can also be fabricated in sections. Separate sections of a hook component can be formed to have different properties and the separate sections can be later assembled.

Various configurations of the engagement and non-abrasive zones 65 and 67 can be utilized to form the multiple property fasteners 60 of the invention. For example, the multiple property fastener 60 can have an engagement zone 65 covering approximately one half of the fastener area 64 in the longitudinal direction 62 and a non-abrasive zone 67 covering approximately the other half of the fastener area 64 in the longitudinal direction 62. Similarly, the multiple property fastener 60 can have an engagement zone 65 covering approximately one half of the fastener area 64 in the lateral direction 63 and a non-abrasive zone 67 covering approximately the other half of the fastener area 64 in the lateral direction 63. Alternatively, the multiple property fastener 60 can have an engagement zone 65 covering a central portion of the fastener area 64 and a non-abrasive zone 67 covering a perimeter that surrounds the central portion of the fastener area 64. The multiple property fasteners 60 can also have more than two zones of fastening materials. For example, the multiple property fastener 60 can be considered to be divided into a top portion, a longitudinal center portion and a bottom portion. An engagement zone of a first mechanical fastening material can cover the center portion and non-abrasive zones 67 of a second mechanical fastening material can cover the top and bottom portions. In another example, the multiple property fastener 60 can be considered to be divided into an exterior portion, a lateral center portion and an interior portion. An engagement zone 65 of a first mechanical fastening material can cover the center portion and non-abrasive zones of a second mechanical fastening material can cover the exterior and interior portions.

FIG. 4 representatively depicts various examples of multiple property fasteners 60 of the invention. FIG. 4 includes some of the configurations of engagement zones 65 and non-abrasive zones 67 described in the preceding paragraph. The multiple property fasteners 60 can be used with prefastened or conventional absorbent articles. However, the multiple property fasteners 60 provide benefits particular to prefastened articles as will be described herein. In FIG. 4, the fasteners are shown as having different patterns of zones of "higher engagement" and "non-abrasive" hooks. If the design of the absorbent article is such that the most likely portion of the fastener to come into contact with the skin is the top of the fastener (top in the longitudinal direction 62 of the fastener), the non-abrasive hooks can be formed in a top/upper zone of the fastener (Example "A" in FIG. 4). In order to provide a fastener having non-abrasive and skin-friendly properties in the portions that may encounter both the waist and legs of the wearer, the configuration of hooks depicted in Example "H" of FIG. 4 may be appropriate. Non-abrasive hooks can also be provided around the entire perimeter of the fastener as depicted in Example "F". Desirably, the higher engagement hooks give the fastener sturdy engagement properties while the non-abrasive hooks impart sensitivity to the fastener so that skin irritation is reduced or avoided.

Figure 6:
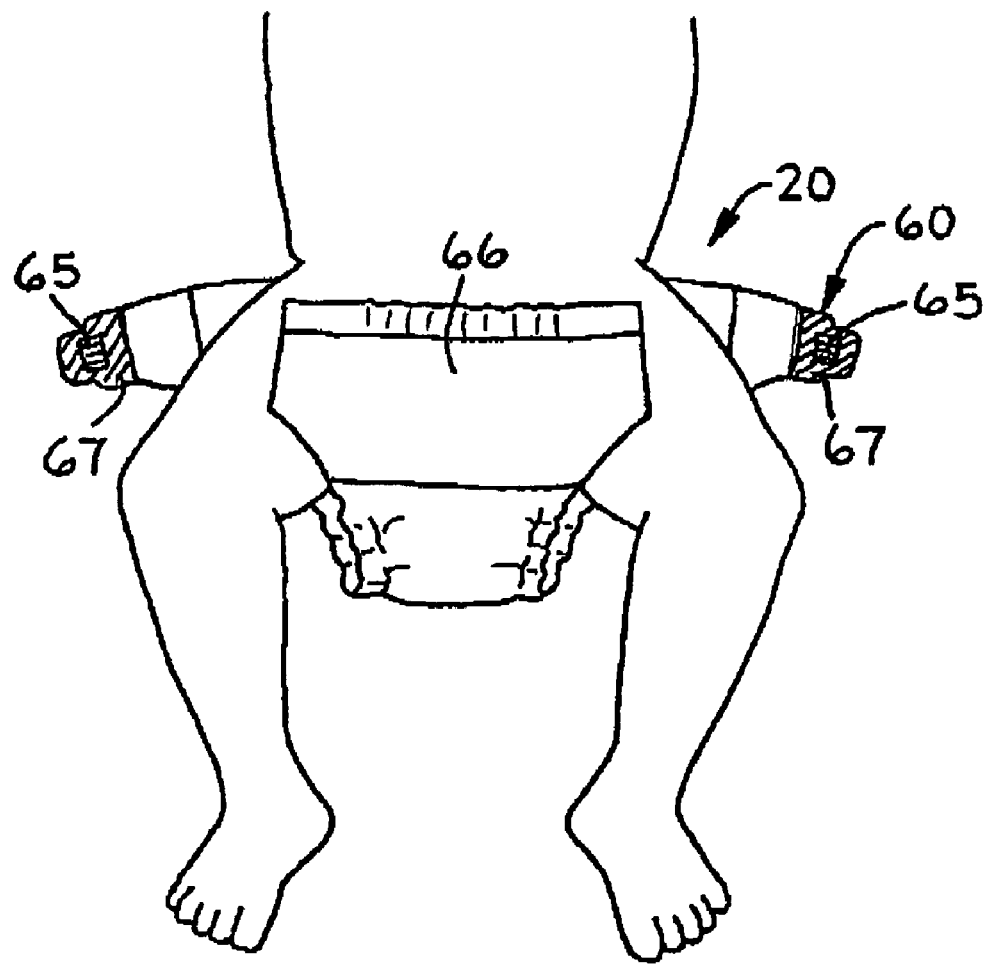
FIG. 6 representatively shows a perspective view of an absorbent article of the invention being applied to a child; in particular, the Figure is intended to illustrate how the skin of the wearer or caregiver can be exposed to the fastening material of the article.
Figure 7:
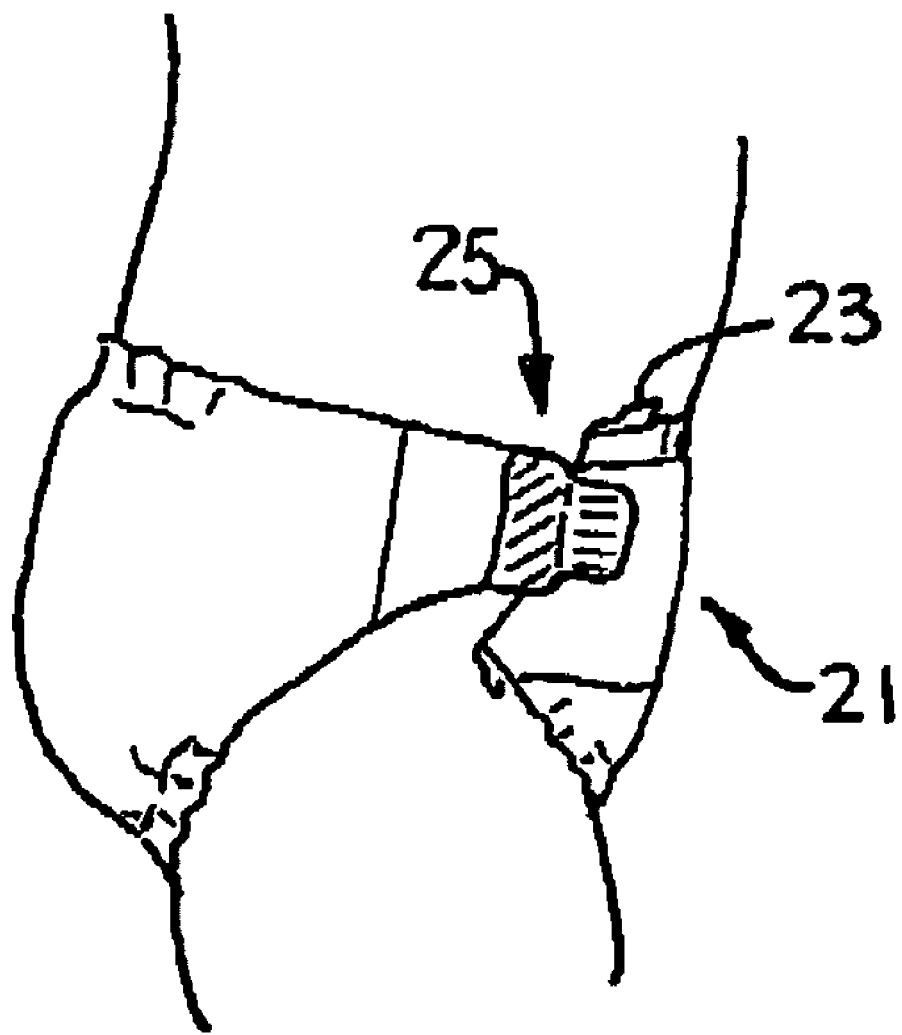
FIG. 7 representatively shows a side view of an absorbent article as worn by a child; in particular, the Figure is intended to illustrate how portions of an article can become wrinkled or crushed in use in such a way that the wearer's skin is inadvertently exposed to fastening material.

Examples of how absorbent articles, particularly diapers, are applied and worn are represented in FIGS. 6 and 7. FIG. 6 depicts a prefastened article of the invention that has been opened-up for application as a conventional diaper. When the articles of the invention are applied or removed as conventional diapers, the multiple property fasteners 60 have the potential to come into contact with both the abdomen and legs of the wearer. The likelihood of contact with the skin of the wearer increases as the age and associated physical activity of the wearer increase. Hence, as in the configuration shown in FIG. 6, the desirability of having the engagement zone 65 located in the center of the multiple property fastener 60 and surrounded by the non-abrasive zone 67 can be understood. Such a configuration is also illustrated by Example "F" of FIG. 4. Depending on the particular shape and design of the multiple property fastener 60, Examples "G", "H" and "I" of FIG. 4 may also be appropriate to minimize the effect of exposure of the fastener to skin.

FIG. 7 depicts a conventional diaper 21 in a side view as it is being worn. FIG. 7 illustrates how a front ear portion or region 23 of a diaper can become crumpled or folded in during use. Such crumpling or folding in use can occur in such a way that the wearer's skin is inadvertently exposed to the engaging material of the fasteners of the diaper 21. This hip region 25 of the wearer's skin is already susceptible to irritation from the inherent friction experienced by wearing an absorbent article. The multiple property fasteners 60 of the invention can beneficially reduce or eliminate the irritation experienced in the hip region 25 of the wearer. For example, multiple property fasteners 60 having the configurations illustrated by Examples "D-I" of FIG. 4 would be suitable for a fastener used in a conventional diaper 21 design.

The multiple property fasteners 60 of the invention are also oversized to provide stability between the front waist region 22 and the back waist region 24 and to maintain the article 20 in a pant-like, prefastened configuration. The multiple property fastener 60 can also be oversized to provide a single source of closure for the pant-like, prefastened article 20. Prior prefastened articles have relied on secondary fasteners, side seams and passive bond areas to provide their prefastened configuration (See e.g. U.S. Pat. No. 6,287,287 issued to Elsberg on Sep. 11, 2001). A prefastened article having a single source of closure is more simply and efficiently manufactured than a prefastened article having secondary fasteners, side seams or passive bond areas. When secondary fasteners, side seams or passive bond areas have to be incorporated into a high speed web of nonwoven materials that are formed into individual absorbent articles, processing difficulties can be encountered because additional materials are used. Further, the portions of the article being prefastened together (typically the front waist region 22 and back waist region 24) have to be registered properly in relation to each other prior to fastening; this registration can be challenging. The single source of closure/prefastening provided by the oversized, multiple property fasteners 60 of the invention reduce or eliminate such difficulties.

Figure 8:
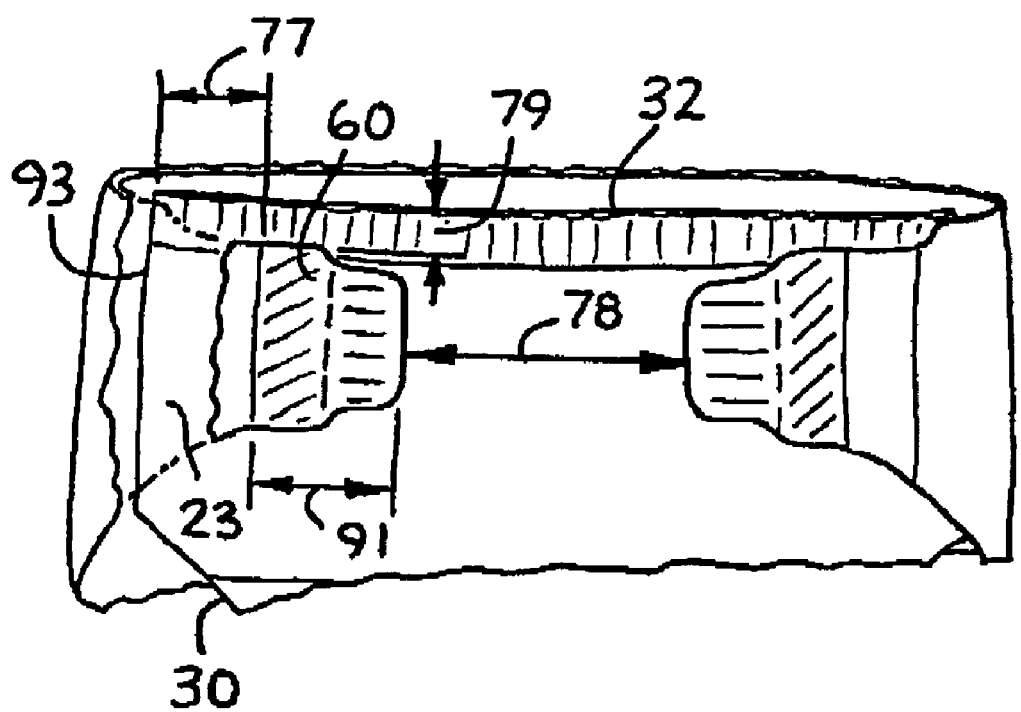
FIG. 8 representatively shows a partial plan view of a prefastened absorbent article of the invention in a fist position in order to illustrate the relationship between the multiple property fasteners of the invention and the front waist region of the article.

The hook and tape fasteners provided on currently available diapers cannot simply be positioned in a front waist region 22 of a diaper to provide a pant-like, prefastened configuration. Conventional fasteners do not have the proper dimensions to provide a functional prefastened article. Experiments were conducted to illustrate the deficiencies of conventional fasteners and the benefits of the oversized, multiple property fasteners 60 of the present invention. The experiments entailed measuring the position of the fastening material in relation to the edges of currently available diapers and prefastened articles of the invention. FIG. 8 representatively depicts the measurements taken. Each of the tested articles was configured so that the fasteners were positioned similarly in the front waist region 22 of the articles. Specifically, the fasteners were placed on the attachment zone areas so that the lateral edges of the left and right fasteners were spaced 2.5 inches (6.35 cm) apart; this spacing is illustrated by reference numeral 78 in FIG. 8. By keeping the fastener spacing the same for each article tested, the waist opening would be the same for each article. When the size of the waist openings are the same, the articles can be applied more similarly and consistently. The tested articles each had fasteners of different dimensions; specifically, the tested fasteners differed in the length of mechanical fastening material 91 in the lateral direction of the fastener 63.

After positioning of the fasteners in the front waist region 22 of the articles, the "prefastened" articles were pulled up (like a training pant) onto a silicone gel mannequin sized for infants weighing 16 to 28 lbs. The articles were pulled upward by alternating pulling from the front, back and sides of the articles as is typically done by consumers. After application, additional measurements were made: the distance that the front ear portion 23 rolled inward (toward the interior surface 34) on both the left and right sides was measured. Whether or not the fastening material of the fasteners became exposed to the surface of the mannequin was also recorded. The measurements for two commercially available diapers and five experimental articles are provided in Table 1. below.

TABLE 1

| Article | Distance between edge of fastening material and edge of front ear portion (mm) | Distance front ear portion was folded in after article was pulled up (mm) LEFT Side | Distance front ear portion was folded in after article was pulled up (mm) RIGHT Side | Fastening material exposed? |
|---|---|---|---|---|
| HUGGIES ULTRATRIM Diaper (Step Size 4) | 59 | 30 | 132 | Yes |
| PAMPERS PREMIUM Diaper (Step Size 4) | 81 | 100 | 93 | Yes |
| Article "A" (25 mm of hook) | 125 | 57 | 110 | No |
| Article "B" (64 mm of hook) | 50 | 65 | 70 | No |
| Article "C" (76 mm of | 38 | 50 | 65 | No |

TABLE 1-continued

| Article | Distance between edge of fastening material and edge of front ear portion (mm) | Distance front ear portion was folded in after article was pulled up (mm) LEFT Side | Distance front ear portion was folded in after article was pulled up (mm) RIGHT Side | Fastening material exposed? |
|---|---|---|---|---|
| hook) Article "D" (89 mm of hook) | 25 | 0 | 0 | No |
| Article "E" (101 mm of hook) | 12 | 0 | 0 | No |

For Articles "A" through "E" in Table 1., the length of the fastening material in the fastener lateral direction 63 is indicated below the identification of the Articles in the table. For the commercially available samples, the length of the fastening material in the fastener lateral direction 63 was as follows: (1) HUGGIES ULTRATRIM diaper—25 mm; and (2) PAMPERS PREMIUM diaper—12 mm. For Articles "A" through "E" in Table 1, the length of the fastening material in the fastener longitudinal direction 62 was 52 mm. The commercially available samples had lengths of fastening material in the fastener longitudinal direction 62 as follows: (1) HUGGIES ULTRATRIM diaper—58 mm; and (2) PAMPERS PREMIUM diaper—32 mm.

As illustrated by the results in Table 1., the size of the fastener affects the performance of an article in a prefastened configuration. When the fasteners are placed 2.5 inches apart (distance indicated by reference numeral "78" in FIG. 8), the fasteners need to have a lateral length 91 of mechanical fastening material greater than about 85 mm (length indicated by reference numeral "91" in the lateral direction 63 of the fastener) to prevent the front ear portion 23 of the article from folding inward during application to a wearer. Depending on the particular dimensions of the chassis of a prefastened absorbent article, it may be desirable to prefasten the fasteners with a spacing different than 2.5 inches; for example, it may be desirable to space the fasteners about 3.5 inches (8.9 cm) apart. Different fastener spacings will result in fasteners needing to have a different length in the lateral direction of fastening material 91 to prevent folding of the front ear portion 23. Typically, it is desirable to locate the fasteners within about 5.5 inches (14 cm) of each within an engagement zone that includes a mating engagement material or the outer cover/backsheet material. Preferred spacing 78 between the fasteners can depend on the size and overall design of the article.

Performance of the experiments described-above also revealed that it is desirable to have the mechanical fastening material come within about 1 inch (2.54 cm) of the edge 93 of the front ear portion 23. The distance between the mechanical fastening material and the edge 93 of the front ear portion 23 is indicated in FIG. 8 by reference numeral "77". When the fastening material is within about 1 inch of the edge 93, the front ear portion 23 does not fold inward when the article is applied to a wearer. With conventional diapers, it is not possible to locate the fasteners so that mechanical fastening material on the fastener 60 is within about 1 inch of the edge of the front ear portion of the diaper.

The experiments summarized in Table 1 above demonstrate the dimension of the oversized multiple property fasteners 60 in the fastener lateral direction 63. The dimension of the oversized multiple property fasteners 60 in the fastener longitudinal direction 62 is also relevant. If the oversized multiple property fastener 60 does not have sufficient length in the fastener longitudinal direction 62, the waist edge 32 of the article will roll/fold inward. Desirably, the oversized multiple property fastener 60 has a length in the fastener longitudinal direction 62 sufficient to bring the edge of the fastener within about 1 inch (2.54 cm) of the waist edge 32 of the article. The distance between the oversized multiple property fastener 60 and the waist edge 32 is indicated in FIG. 8 by reference numeral 79. Generally speaking then, the oversized multiple property fastener 60 has a top edge that is generally aligned with a waist edge 32 of the article. While waist edge 32 folding was not measured for the articles identified in Table 1., for each of the tested articles the fastener was within about 1 inch of the waist edge. Therefore, it is possible to locate fasteners on conventional diapers within about 1 inch of the waist edge. The maximum length of a fastener in the fastener longitudinal direction 62 will depend on the overall size of the article; desirably, however, the fastener is not so long in the fastener longitudinal direction 62 that the fastener occludes or covers up the leg opening of the article.

Further examples of oversized multiple property fasteners 60 have been identified. The determination of the dimension of the oversized multiple property fastener 60 in the fastener lateral direction 63 begins with measurement of the width of the chassis in the front waist region 32. For prefastened diapers sized for infants/children weighing 22 lbs. to 37 lbs. (Size 4-type diaper) the chassis width is 244 mm; for prefastened diapers sized for infants/children weighing 27 lbs. to 45 lbs. (Size 5-type diaper) the chassis width is 290 mm. When a fastener spacing of 3.5 inches (89mm) is desired, the necessary length of the fastener 60 in the lateral direction 63 can be calculated. For the first size of prefastened diapers, the oversized multiple property fastener 60 needs to have a length of from about 53 mm to about 78 mm in the lateral direction 63 to bring the fastening material to within about 1 inch of the edge 93. For the larger size of prefastened diapers, the oversized multiple property fastener 60 need to have a length of from about 70 mm to about 95 mm in the lateral direction 63 to bring the fastening material to within about 1 inch of the edge 93.

Therefore, it is desirable for the fasteners 60 of the invention to have dimensions sufficient for the fasteners 60 to provide the prefastened configuration of the absorbent articles into which the fasteners 60 are incorporated.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A pant-like, prefastened, disposable absorbent article including an absorbent, a front waist region, a back waist region, a crotch region that extends between and connects the waist regions, a longitudinal direction, a lateral direction, an exterior surface, an interior surface opposite the exterior surface, a pair of laterally opposed side edges and a pair of longitudinally opposed waist edges, the absorbent article further comprising:

a multiple property fastener attached in one of the front waist region and the back waist region, the multiple property fastener comprising at least two zones, at least one engagement zone of a first mechanical fastening material and at least one non-abrasive zone of a second mechanical fastening material wherein the first mechanical fastening material is comprised of a polymeric material selected to have a flexural modulus greater than about 30 kilopounds per square inch and the second mechanical fastening material is comprised of a polymeric material selected to have a flexural modulus between about 7 kilopounds per square inch and about 30 kilopounds per square inch.

2. The absorbent article of claim 1, wherein the multiple property fastener defines a fastener longitudinal direction, a fastener lateral direction and a fastener area, and there is one said engagement zone covering one half of the fastener area in the fastener longitudinal direction and there is one said non-abrasive zone covering the other half of the fastener area in the fastener longitudinal direction.

3. The absorbent article of claim 1, wherein the multiple property fastener defines a fastener longitudinal direction, a fastener lateral direction and a fastener area, wherein there is one said engagement zone covering one half of the fastener area in the fastener lateral direction and there is one said non-abrasive zone covering the other half of the fastener area in the fastener lateral direction.

4. The absorbent article of claim 1, wherein there is one said engagement zone covering a central portion of the fastener area and there is one said non-abrasive zone covering a perimeter that surrounds the central portion of the fastener area.

5. The absorbent article of claim 1, wherein the fastener has a top portion, a longitudinal center portion and a bottom portion and there is one said engagement zone covering the center portion and the at least one said non-abrasive zone comprises non-abrasive zones covering the top portion and the bottom portion.

6. The absorbent article of claim 1, wherein the fastener has an exterior portion, a lateral center portion and an interior portion and there is one said engagement zone covering the center portion and the at least one said non-abrasive zone comprises non-abrasive zones covering the exterior portion and the interior portion.

7. The absorbent article of claim 1, wherein the first mechanical fastening material is made from a polypropylene copolymer.

8. The absorbent article of claim 1, wherein the second mechanical fastening material is made from a polymer selected from elastomeric thermoplastic polymers and metallocene catalyzed polymers.

9. The absorbent article of claim 1 wherein the absorbent article further includes an engagement surface on the exterior surface that extends to form a pair of front ear portions.

10. The absorbent article of claim 9 wherein the engagement surface is a loop material.

11. The absorbent article of claim 9 wherein the engagement surface is an outer cover material.

12. The absorbent article of claim 9 wherein the front ear portion has an edge and the fastener area of the multiple property fastener is within about 2.54 cm of the edge of the front ear portion.

13. The absorbent article of claim 1 wherein the multiple property fastener is engageable into the front waist region of the article.

14. The absorbent article of claim 1 wherein the multiple property fastener is engageable into the back waist region of the article.

15. The absorbent article of claim 1 wherein the multiple property fastener has a top edge that is generally aligned with one of the waist edges of the article.

* * * * *

UNITED STATES PATENT AND TRADEMARK OFFICE
CERTIFICATE OF CORRECTION

PATENT NO. : 7,578,812 B2  Page 1 of 1
APPLICATION NO. : 10/017894
DATED : August 25, 2009
INVENTOR(S) : Datta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 772 days.

Signed and Sealed this

Seventh Day of September, 2010

David J. Kappos
*Director of the United States Patent and Trademark Office*